(12) United States Patent
McDonald (10) Patent No.: US 9,629,692 B2
(45) Date of Patent: Apr. 25, 2017

(54) DENTAL MATRIX BAND RETAINER

(71) Applicant: DENTSPLY International Inc., York, PA (US)

(72) Inventor: Simon P. McDonald, Katikati (NZ)

(73) Assignee: Dentsply Sirona, Inc., York, PA (US)

( * ) Notice: Subject to any disclaimer, the term of this patent is extended or adjusted under 35 U.S.C. 154(b) by 0 days.

(21) Appl. No.: 14/428,639

(22) PCT Filed: Sep. 17, 2013

(86) PCT No.: PCT/US2013/060056
§ 371 (c)(1),
(2) Date: Mar. 16, 2015

(87) PCT Pub. No.: WO2014/047029
PCT Pub. Date: Mar. 27, 2014

(65) Prior Publication Data
US 2015/0216625 A1 Aug. 6, 2015

(30) Foreign Application Priority Data
Sep. 18, 2012 (NZ) ........................................ 602480

(51) Int. Cl.
*A61C 5/12* (2006.01)
*A61C 5/82* (2017.01)
*A61C 5/85* (2017.01)

(52) U.S. Cl.
CPC ................ *A61C 5/125* (2013.01); *A61C 5/82* (2017.02); *A61C 5/85* (2017.02)

(58) Field of Classification Search
CPC ............ A61C 5/12; A61C 5/122; A61C 5/125
See application file for complete search history.

(56) References Cited

U.S. PATENT DOCUMENTS

| | | | | |
|---|---|---|---|---|
| 625,888 A | * | 5/1899 | Leonard ................. | A61C 5/125 433/40 |
| 719,834 A | * | 2/1903 | Mills ...................... | A61C 5/125 433/158 |

(Continued)

FOREIGN PATENT DOCUMENTS

| | | |
|---|---|---|
| DE | 152841 C | 6/1904 |
| FR | 2820024 A1 | 8/2002 |

(Continued)

*Primary Examiner* — Ralph Lewis
(74) *Attorney, Agent, or Firm* — Leana Levin; Douglas J. Hura; David A. Zdurne (57) ABSTRACT

The present invention pertains to a device for retaining a matrix band about at least a portion of a periphery of a tooth to be treated, the device comprising: a first lug to fit on one side of a proximal contact between two teeth; a second lug to fit on the other side of said proximal contact, and a resilient body member connecting between the first lug and said second lug. The body member applies a restorative or clamping force biasing the lugs together against opposed sides of the proximal contact and holds the lugs such that they must be separated to fit over the proximal contact. The first and second lugs are pivotally coupled to the resilient body member to allow the resilient body member to rotate relative to the lugs while providing the clamping force biasing the lugs together.

12 Claims, 7 Drawing Sheets

(56) References Cited

U.S. PATENT DOCUMENTS

| | | | | |
|---|---|---|---|---|
| 1,661,068 A * | 2/1928 | Gaillard | ................. | A61C 5/125 |
| | | | | 433/158 |
| 6,206,697 B1 | 3/2001 | Hugo | | |
| 7,077,651 B2 * | 7/2006 | Anderson | .............. | A61C 5/125 |
| | | | | 433/139 |
| 7,175,432 B2 * | 2/2007 | McDonald | ............. | A61C 5/127 |
| | | | | 433/139 |
| 2013/0344455 A1 * | 12/2013 | Hull | ....................... | A61C 5/125 |
| | | | | 433/29 |

FOREIGN PATENT DOCUMENTS

| | | |
|---|---|---|
| JP | S5632745 A | 3/1981 |
| NZ | 2515528 A | 11/2004 |
| WO | 00/24334 A1 | 5/2000 |

\* cited by examiner

DENTAL MATRIX BAND RETAINER

CROSS-REFERENCE TO RELATED APPLICATIONS

This application is a national phase application of International Application No. PCT/US2013/060056, filed on Sep. 17, 2013, which in turn claims priority to New Zealand Provisional Patent Application No. 602480, filed on Sep. 18, 2012 and New Zealand Non-Provisional Patent Application No. 602480, filed Nov. 22, 2012, the contents of which are all hereby incorporated by reference.

FIELD OF THE INVENTION

The present invention relates to an apparatus for the placement of dental fillings and in particular light curable dental fillings.

SUMMARY OF THE PRIOR ART

The dental profession has moved over the last three or so decades from the use of mercury based fillings to the use of composite resins that are used to provide natural looking fillings. Composite resin is cured by the application of concentrated light. To enable the dental professional to place composite resin fillings matrixes are used. A matrix is a device which wraps around the tooth and acts as a mould to contain the composite resins before they are cured. Matrices are generally formed of plastic or stainless steel and are either circumferential or sectional. Sectional matrices fit only in one proximal area of the tooth while circumferential matrix bands fit around the entire circumference of the tooth. In the prior art, matrixes are secured in place by the use of wedges and/or retainers/clamps. Wedges are generally made of wood or plastic and are placed between the matrix and an adjacent tooth. Wedges are used to hold the matrix against the tooth being filled and to temporarily separate the tooth being filled and the adjacent tooth. Matrix band retainers hold the matrix against the tooth being filled by clamping about either side of the tooth over the matrix.

It is an object of the present invention to provide a new or alternative matrix band securing system of a dental filling placement apparatus, or to at least provide the public with a useful choice.

SUMMARY OF THE INVENTION

In a first aspect the invention may broadly be said to consist in a device for retaining a matrix band about at least a portion of a periphery of a tooth to be treated, the device comprising:
a first lug to fit on one side of a proximal contact between two teeth,
a second lug to fit on the other side of said proximal contact,
a resilient body member connecting between said first lug and said second lug, said body member holding said lugs such that they must be separated to fit over said proximal contact, wherein the body member applies a restorative or clamping force biasing said lugs together against opposed sides of said proximal contact in use, and
each of the first and second lugs pivotally coupled to the resilient body member to allow the resilient body member to rotate relative to the lugs while providing the clamping force biasing the lugs together.

Preferably the first and second lugs are pivotally coupled to respective ends of the body member to enable the body member to rotate about an axis substantially transverse to the sagittal plane of a tooth to be treated in use.

Preferably the body member is a U-shaped spring member having two separate and opposed ends at an opening of the U-shaped member, the spring biasing the two ends together when the ends are separated from an un-deflected position of the spring, each lug pivotally coupled to a respective end of the spring.

Preferably the body member is formed from a nickel-titanium alloy.

Preferably the first and second lugs are releasably coupled to the body member.

Preferably the first and second lugs each comprise a socket for rotatably receiving an associated inwardly extending end of the body member.

Preferably each inwardly extending end of the body member and an inner periphery of the associated lug socket comprise corresponding formations for enabling a releasable engagement between the body end and the lug.

Preferably each end comprises an annular detent about the outer periphery of the end and each lug comprises a corresponding annular rib formed about the inner periphery of the lug socket for engaging the associated detent in use.

Preferably each lug comprises, at the inner periphery of the socket of the lug, one or more flat surfaces for defining pivotal position limits, and wherein the corresponding end of the body member comprises one or more flat surfaces at the outer periphery for engaging with the corresponding flat surfaces of the socket when the end is received within the socket and rotated to a pivotal position limit in use.

Preferably the inner periphery of the socket of each lug comprises two flat surfaces separated at less than 180 degrees about the inner periphery to define two pivotal position limits of the body member less than 180 degrees apart during use.

Preferably each lug comprises an abutment surface for abutting against the matrix band at the corresponding side of the tooth in use.

Preferably the abutment surface is contoured to substantially conform to the periphery of corresponding sides of two adjacent teeth and to the inter-proximal space between the teeth in use.

Preferably the abutment surface of each lug comprises an intermediate ridge adapted to engage the inter-proximal space between two teeth in use.

Preferably each lug comprises a channel for receiving a dental wedge in use.

Preferably the channel is formed to conform to the outer periphery of an end of the dental wedge to thereby enable opposing ends of the wedge to be received and retained within the channel of each lug when the lug is located against the matrix band in use and when the wedge is fitted in the inter-proximal space between the opposing sides of the tooth in use.

Preferably each lug is formed from a polymer-based plastics material.

Preferably each lug is formed from a transparent or semi-transparent material.

In a second aspect the invention may broadly be said to consist of a kit of parts for a device for retaining a matrix band about at least a portion of a periphery of a tooth to be treated, the kit of parts comprising:
a first lug to fit on one side of a proximal contact between two teeth, a second lug to fit on the other side of said proximal contact, a resilient body member to connect between said first lug and said second lug, when connected between said first and second lugs, said resilient body member holding said lugs such that they must be separated to fit over said proximal contact, wherein the body member applies a restorative or clamping force biasing said lugs together against opposed sides of said proximal contact in use, and each of the first and second lug members and the resilient body member adapted to be pivotally coupled together, to allow the resilient body member to rotate relative to the lug members in use while providing the clamping force biasing the lug members together.

Preferably the first and second lugs are adapted to be pivotally coupled to respective ends of the body member to enable the body member to rotate about an axis substantially transverse to the sagittal plane of a tooth to be treated.

Preferably the body member is a U-shaped spring member having two separate and opposed ends at an opening of the U-shaped member, the spring biasing the two ends together when the ends are separated from an un-deflected position of the spring.

Preferably the body member is formed from a nickel-titanium alloy.

Preferably the first and second lugs are adapted to be releasably coupled to the body member.

Preferably the first and second lugs each comprise a socket for rotatably receiving an associated inwardly extending end of the body member.

Preferably each inwardly extending end of the body member and an inner periphery of the associated lug socket comprise corresponding formations for enabling a releasable engagement between the body end and the lug.

Preferably each end comprises an annular detent about the outer periphery of the end and each lug comprises a corresponding annular rib formed about the inner periphery of the lug socket for engaging the associated detent when assembled.

Preferably each lug comprises, at the inner periphery of the socket of the lug, one or more flat surfaces for defining pivotal position limits, and wherein the corresponding end of the body member comprises one or more flat surfaces at the outer periphery for engaging with the corresponding flat surfaces of the socket when the end is received within the socket and rotated to a pivotal position limit in use.

Preferably the inner periphery of the socket of each lug comprises two flat surface separated at less than 180 degrees about the inner periphery to define two pivotal position limits of the body member less than 180 degrees apart during use.

Preferably each lug comprises an abutment surface for abutting against the matrix band at the corresponding side of the tooth in use.

Preferably the abutment surface is contoured to substantially conform to the periphery of corresponding sides of two adjacent teeth and to the inter-proximal space between the teeth in use.

Preferably the abutment surface of each lug comprises an intermediate ridge adapted to engage the inter-proximal space between two teeth in use.

Preferably each lug comprises a channel for receiving a dental wedge in use.

Preferably the channel is formed to conform to the outer periphery of an end of the dental wedge to thereby enable opposing ends of the wedge to be received and retained within the channel of each lug when the lug is located against the matrix band in use and when the wedge is fitted in the inter-proximal space between the opposing sides of the tooth in use.

Preferably wherein each lug is formed from a polymer based plastics material.

Preferably each lug is formed from a transparent or semi-transparent material.

Preferably the kit of parts further comprises a matrix band adapted to extend about a least a portion of a tooth between two opposing sides of the tooth.

Preferably the kit of parts further comprises a dental wedge adapted to be fitted in the inter-proximal space between two teeth.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

The invention consists in the foregoing and also envisages constructions of which the following gives examples only.

BRIEF DESCRIPTION OF THE DRAWINGS

A preferred embodiment of the present invention will now be described with reference to the accompanying drawings in which.

DETAILED DESCRIPTION OF THE PRESENT INVENTION

Figure 1:
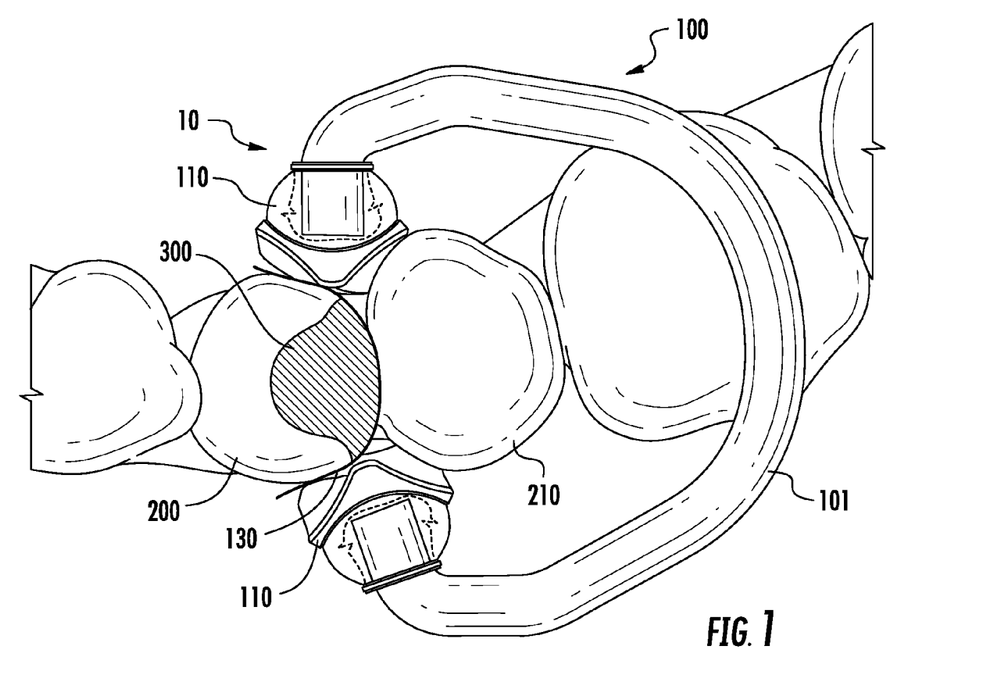
FIG. 1 is an in-situ plan view of the dental contact matrix system according to the invention in use.

Referring to FIG. 1 there is shown a dental contact matrix system comprising a dental matrix band retainer according to a preferred embodiment of the present invention. The dental contact matrix system 10 includes the retainer 100 with a main resilient body member or spring 101 and two lugs 110 attached to ends of the spring 101. A matrix band 130 of the dental matrix contact system is held in place against a tooth 200 by lugs 110. Optionally an elastic dental wedge (not shown) is positioned under the two lugs 110 and the spring 101 and between teeth 200, 210 to further contain the matrix in place. The spring 101 is formed so that the lugs 110 when coupled to the ends of the spring 101 are biased towards one another to thereby clamp about the respective tooth/teeth to hold the associated matrix 130 in place. The matrix 130 helps form a mould to contain composite resin filling 300 during the curing stage of a dental filling procedure on a tooth 200. The lugs 110 are rotatably coupled to the spring 101 to enable rotational adjustment of the spring's position during use to minimize the spring's obstruction on the dental professional during the procedure. Once clamped in position, a dental practitioner may pivot the spring 101 from one side of the filling area 300 to the other side of the filling area, without releasing the matrix band and/or without moving the lugs. Preferably the lugs are also detachable from the spring to enable cleaning and/or replacement of the lugs 110 post procedure if necessary.

Figure 2:
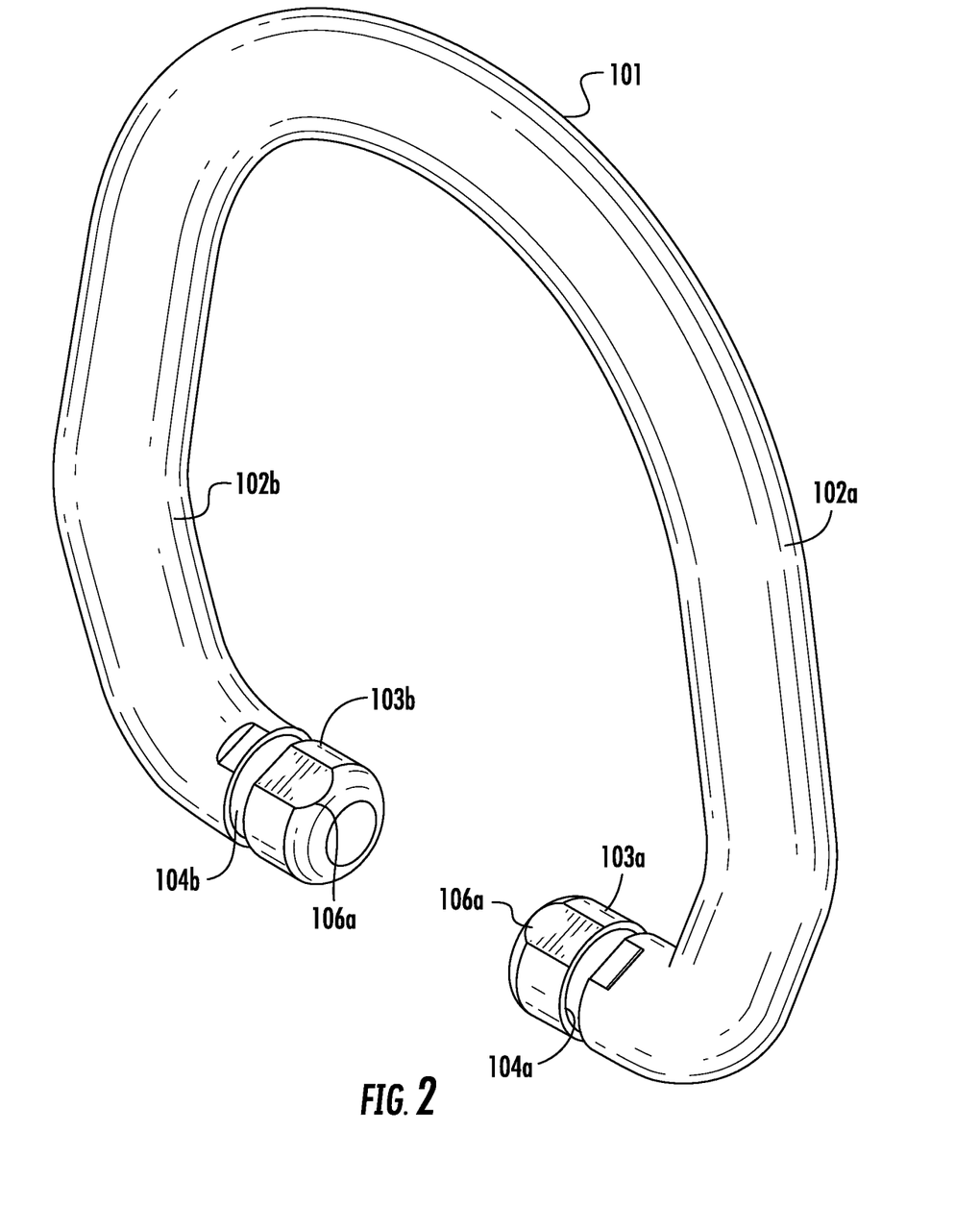
FIG. 2 is an isometric view of a preferred form spring of the dental contact matrix system of the invention.
Figure 3:
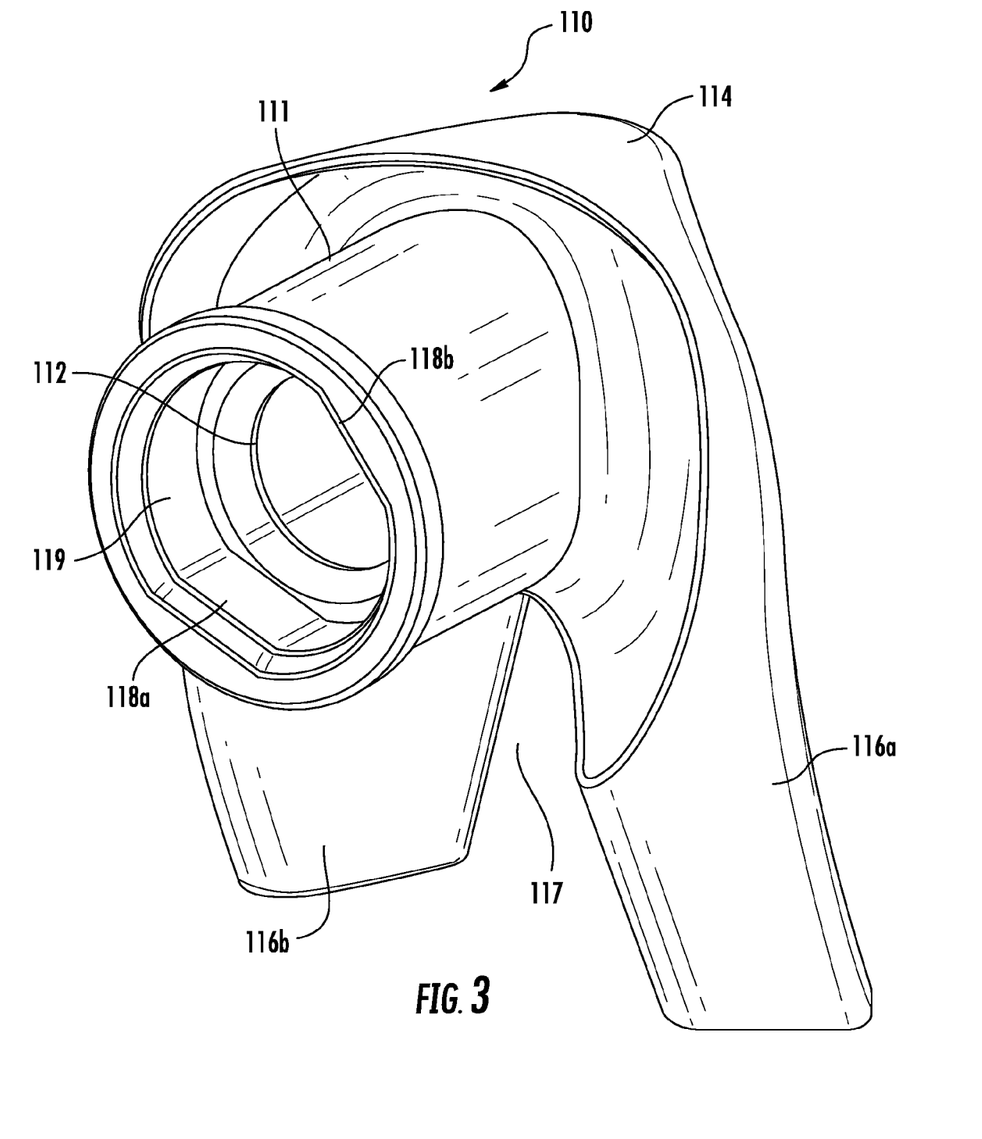
FIG. 3 is an isometric socket end view of a preferred form lug of the dental contact matrix system of the invention.

Referring to FIG. 2, the spring 101, in the preferred embodiment is substantially semi circular or U-shaped in plan view with two inwardly projecting ends 103a/b. The spring 101 has two arms 102a, 102b that curve round and terminate with the inwardly facing but separated ends 103a, 103b. The arms 102a, 102b require a force to push them apart to deflect the spring, and are resilient to bias the ends 103a, 102b towards one another from a deflected position towards an un-deflected position. The two ends 103a, 103b are substantially aligned when they have been fitted on either side of a tooth 200 in the preferred embodiment. A groove or detent 104a, 104b is circumferentially provided at each end 103a, 103b of the arms 102a, 102b to enable the corresponding lug 110 to be coupled therewith. A corresponding rib (112 in FIG. 3) of each lug 110 engages the detent 104 to couple the parts together. Spring 101 is formed of resiliently flexible material such as a plastics or metal material. In the preferred embodiment the spring 101 is formed from a metal based material such as a nickel-titanium alloy, stainless steel or spring steel. To mount the retainer 100, a dental professional or other user would, using dental forceps or another similar tool, separate the arms 102a, 102b against the bias of the spring to open up the ends 103a, 103b (with lugs 110 connected therewith) further and mount the retainer 100 around the desired tooth 200. Releasing the spring 101 would then cause the lugs 110 to clamp against the tooth 200 as the ends 103a, 103b return towards their relaxed and undeflected state.

Figure 6:
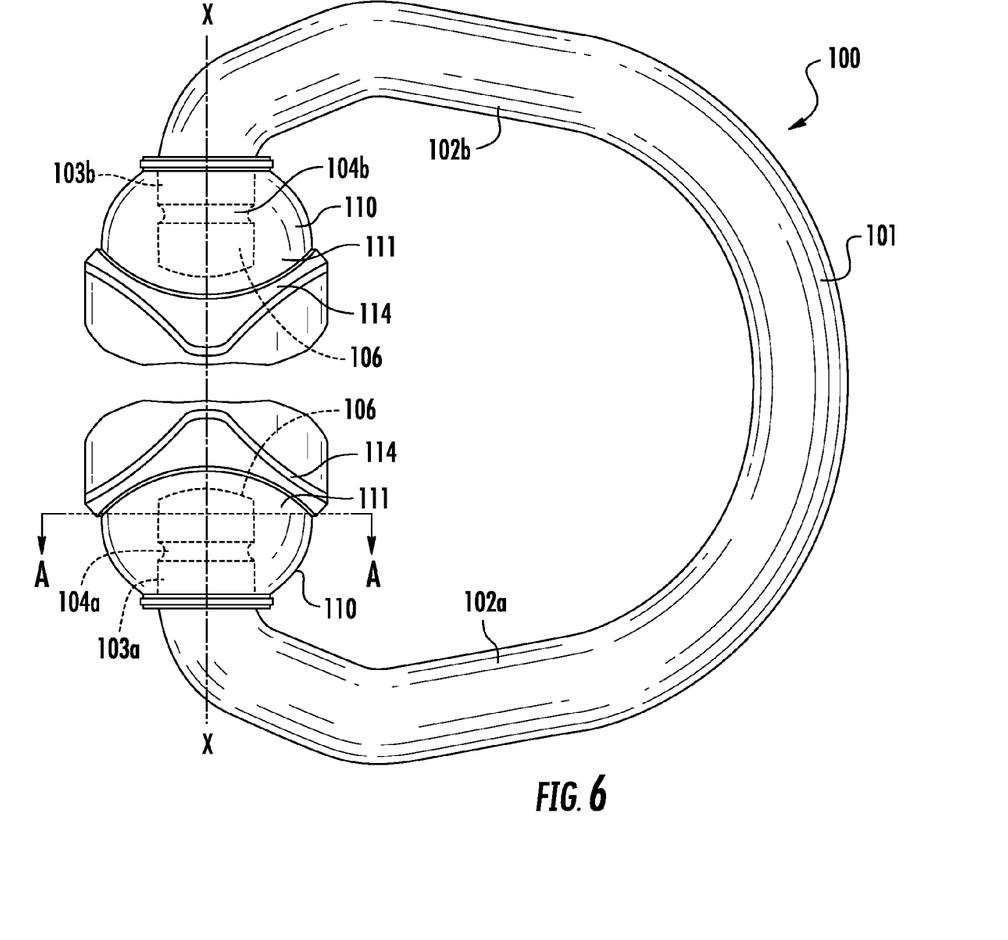
FIG. 6 is a plan view of the assembled retainer of FIG. 5.
Figure 7:
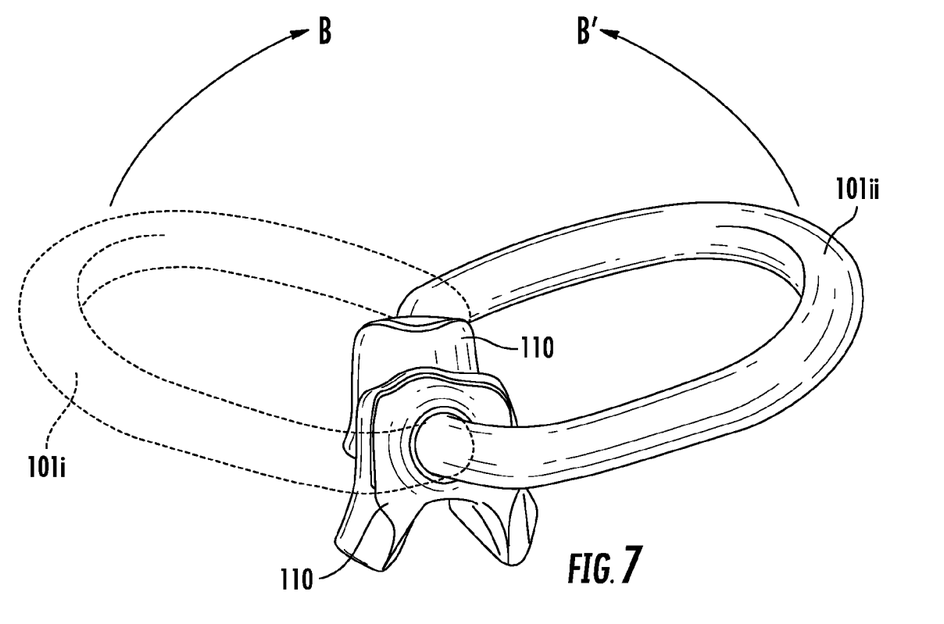
FIG. 7 is a three-dimensional view of the retainer of FIG. 5 showing pivotal position limits of the spring.

Referring to FIGS. 3 to 8, each lug 110 comprises a socket 111 having an open end for receiving and connecting the lug 110 to the respective end 103 of the spring 101, and a closed end terminating in an abutment portion 114 of the lug 110. Preferably each lug is releasably attachable to the spring 101. Each lug 110 comprises a rib 112 at the inner periphery of the socket 111 for releasably coupling to the detent 104 of the corresponding spring end 103, via an interlocking arrangement for example. In the preferred embodiment, the substantially annular outer periphery of end 103 of spring 101 is rotatably received within the substantially circular inner periphery of socket 111 to thereby enable rotational adjustment of the position of the spring 101 relative to the lugs 110 and patient's teeth during use of the device. This enables the spring 101 in use to be located above neighboring teeth to the tooth being filled and also the path and position of the spring 101 to be altered by the dental professional by pivoting or rotating the spring about the lugs to allow unobstructed viewing of the tooth being filled during the procedure. It will be appreciated that in alternative embodiments, other mechanical configurations may be incorporated for rotatably coupling the lugs 110 with the ends 103a, 103b of the spring 101. As shown in FIGS. 6 and 7, the spring 101 is capable of rotating about an axis X when coupled to the lugs 110. In use, the axis of rotation is transverse to the sagittal plane of the tooth 200. This enables clockwise, S, and anticlockwise, S', rotation of the spring 101 to alter the resting position of the spring during use.

In one embodiment, the inner peripheral wall 119 of socket 111 is formed with two flats 118a, 118b configured to engage one or more of two corresponding flats 106a, 106b at the outer periphery of the associated end 103a/b of the spring 101 during use. The flats 118a, 118b provide pivotal position limits/stops for the spring 101 relative to the socket 111. The socket or flat portions or both may be formed from a resilient material that allows the socket to deform during rotation of the spring 101. In the preferred embodiment, the flats 118a, 118b and 106a, 106b are radially spaced at less or more than 180 degrees apart to provide a practical range of motion (of less or more than 180 degrees as shown in FIG. 7) for the spring 101 in use. In use, rotation of the spring causes the flat 106a/b on the spring ends to move in and out of engagement with the corresponding flats 118a/b in the socket of the lugs. Rotational motion is mechanically interrupted by the engagement of one of the spring flats 106a/b with one of the socket flats 118a/b to indicate pivotal limits of the spring 101.

Figure 8:
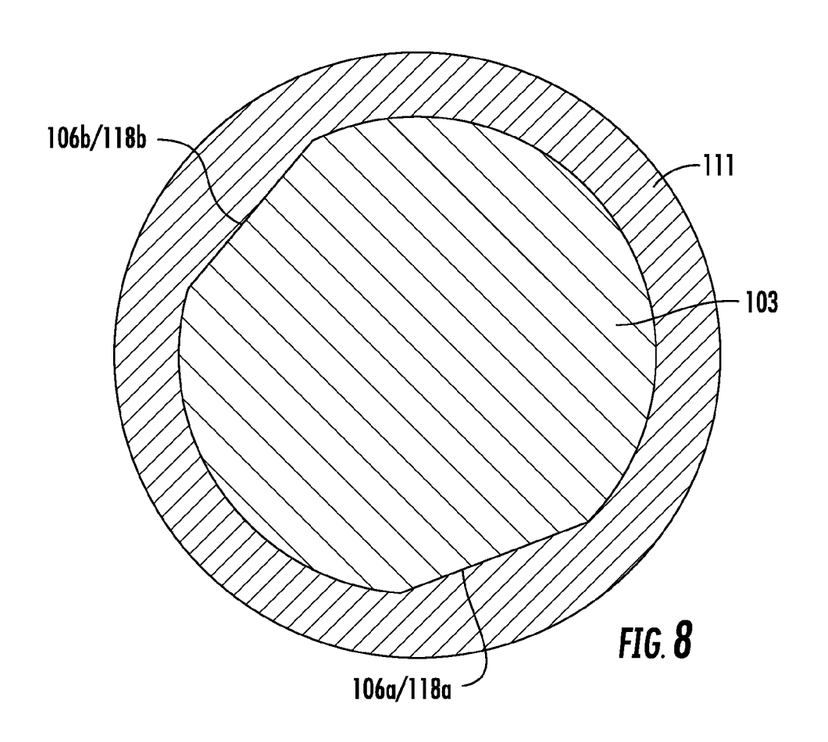
FIG. 8 is a cross-sectional view of the retainer through line A-A' of FIG. 6.

In the embodiment shown, there are three possible indexed positions provided by the spring end and socket flats 106, 118. In a first position, both spring end flats 106a, 106b engage both socket flats 118a, 118b. This is shown in the cross-sectional image taken across line A-A', where the connection between end 103a and lug 110 shows the flat pairs 106a, 106b and 118a, 118b engaged/aligned. This position is achieved when the spring 101 is rotated to an intermediate position between the pivotal limits 101i and 101ii shown in FIG. 7. As the spring 101 is rotated clockwise from this position, flats 106a/118a and flats 106b/118b disengage. The annular portion of the outer periphery of the spring end causes the resilient flats 118a/b at the inner periphery 119 of the socket 111 to deform. This creates a friction fit that enables the pivotal position of the spring 101 to be adjusted in the clockwise direction towards the pivotal limit 101ii. Continued rotation in the clockwise direction eventually causes spring end flat 106b to engage socket flat 118a indicating to a dental professional the pivotal position limit of the spring 101ii. This prompts the professional to suspend further rotation of the device in the clockwise direction. Rotation of the spring 101 in the anticlockwise direction from limit 101ii and from the intermediate position (where both flat pairs are engaged) will also cause deformation of the socket flats 118a, 118b (for adjustment of the pivotal position in this direction) until the pivotal limit 101i is reached (with flats 106a/118b engaging) prompting the dental professional to suspend rotation.

It will be appreciated any number of flats may be formed at any location on the inner periphery 119 of the socket 111 and/or outer periphery of the ends 103a, 103b for defining pivotal positions of the spring 101 as may be required/desired by the dental professional. In alternative embodiments, other mechanical configurations for providing pivotal position limits for the spring 101 may be incorporated and may define a discrete number of positions and/or positional limits at an infinite number of positions as in a high friction fit arrangement for example. Alternatively, the spring 101 may simply freely rotate about the lugs 101 and rest on the patient's teeth at either pivotal limit available to the dental professional during use without the aid of additional mechanical means for indicating pivotal position limits.

Figure 4:
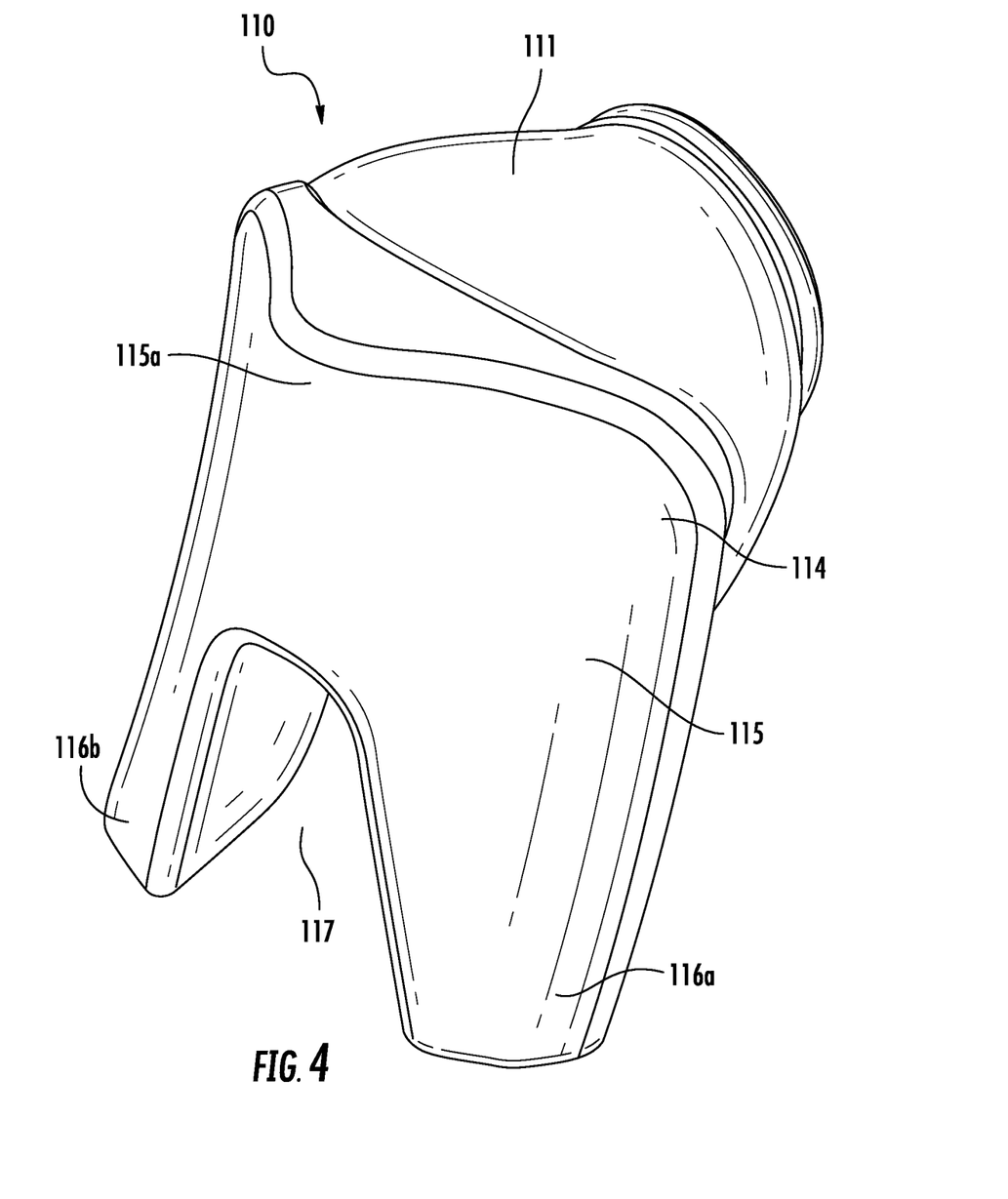
FIG. 4 is an isometric abutment end view of the lug of FIG. 3.
Figure 5:
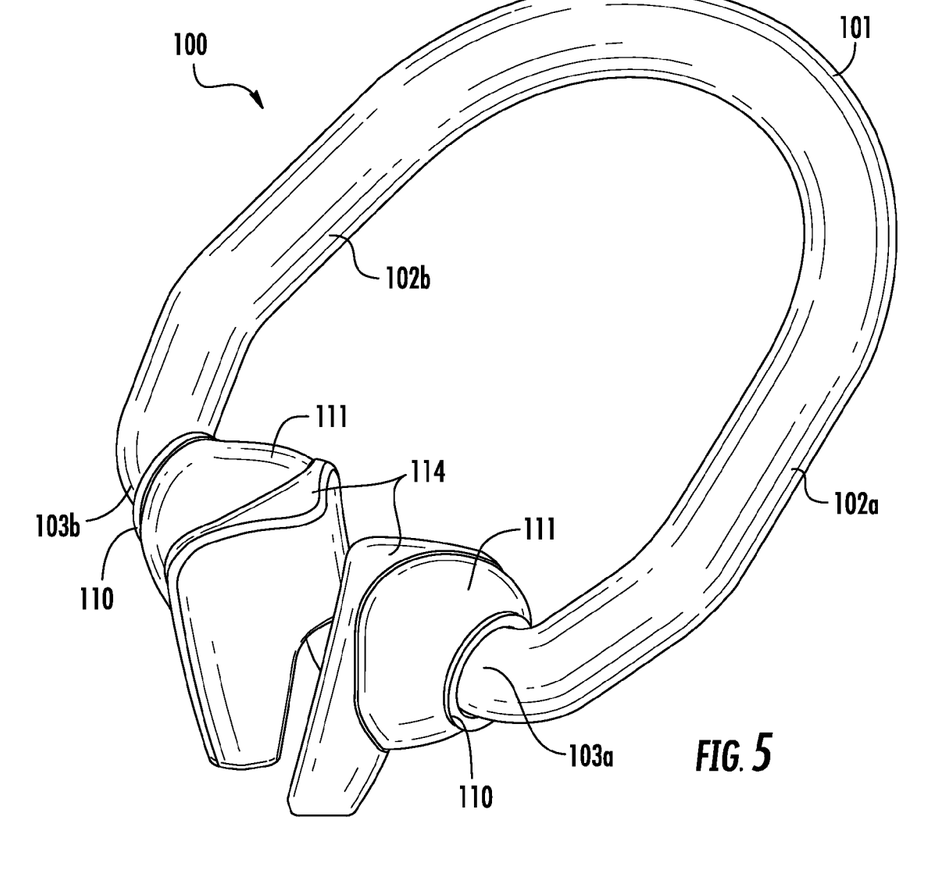
FIG. 5 is an isometric view of spring and lugs (retainer) of FIGS. 1-3 coupled.

Referring to FIG. 4, the abutment portion 114 of lug 110 is formed to bear against the dental contact matrix in use at the appropriate location of the corresponding tooth 200, and preferably at the inter-proximal space between two adjacent teeth 200, 210. A face 115 of the abutment portion 114 abuts the tooth 200 being filled and/or the matrix band 130 and the neighboring tooth 210 in use. The face 115 is concave to preferably conform to the inter-proximal space between the teeth. Preferably the face includes a ridge 115a at an intermediate portion of the face 115 for projecting into and against the inter-proximal space between the two teeth 200, 210. In use, one lug 110 is assembled to fit on the lingual side of the tooth 200 and the other lug 110 on the buccal side of the tooth 200. Each lug 110, and in particular the abutment portion 114 may be symmetrical on either side of the ridge 115a or may be asymmetrical as required by the corresponding teeth 200/210 lingual/buccal side profiles.

The abutment portion 114 of each lug 110 preferably further comprises a pair of legs 116a, 116b extending from the abutment face 115 under the socket 111 and corresponding teeth in use. The legs 116a, 116b form a recessed channel 117 formed to receive, or receive and retain, a portion of a dental wedge therein. In the preferred embodiment, the channel 117 is V-shaped for receiving the tapered end of a dental wedge. In use, a dental wedge can be fitted to the dental contact matrix system after fitting the retainer 100 to the patient's tooth 200, by placing (and preferably stretching) the wedge across the inter-proximal space between the lingual and buccal sides of the associated teeth, and retaining the wedge ends in the channel portion 117 of each lug 110. This arrangement further secures the dental matrix 130 and lugs 110 in place. Alternatively, the wedge may be positioned before the retainer 100 is positioned for use.

The wedge preferably comprises a one piece member of elastic material such as plastic or other suitable material. Preferably a polymer based material, such as polypropylene or acetal is used as it has suitable elasticity properties but any other material that has like elasticity properties would be suitable. The cross section of the wedge may be an equilateral triangle or any triangular or other shape suitable to fit in the inter-proximal space. The channel 117 of the lugs is preferably formed to correspond to the shape of the dental wedge used. A retainer according to the present invention may be used with or without a dental wedge. In a less preferred embodiment, the lugs do not comprise channels 117 on the abutment portion 114.

The lugs 110 are preferably made of injection molded polymer-based plastics material but could be made of any suitable plastics material or ceramic material or a metal based material such as stainless steel. The abutment portion 114 and socket 111 are preferably molded as a single component, but may be over-molded or otherwise separately formed and adhered/coupled to one another. In the preferred embodiment the lugs 110 are transparent or semi-transparent to enable light to pass through the lugs to cure the composite resin filling. A light shined from above the lugs will preferably be reflected towards the filling to be cured.

The dental contact matrix system 10 of the present invention can be assembled and the spring 101 can be pivoted about the lugs 110 such that the matrix is curved into the U-shaped retainer or towards a centre of the U-shape seen generally in FIG. 1, or with the matrix curved away from the U-shape. The ability to pivot the spring 101 makes it easier for the dental professional to use the system during a procedure on a respective tooth. The ability to pivot the spring 101 also allows for easy filling of two adjacent teeth where two retainers 100 will have to be placed. In this case, one retainer can be pivoted mesially and the other retainer can be pivoted distally (in opposite directions away from each other), thereby allowing for a central area free of retainers for the dental professional to work on. It also provides for convenient stacking of multiple retainers 100 for storage purposes. Furthermore, the ability to releasably couple the lugs 110 to the spring 101 enables a dental professional to separate the lugs 110 from the spring 101 after use to clean and/or replace the lugs 110 before the next dental procedure.

The matrix 130 is formed of materials such as acrylic, thermoplastic or stainless steel. Matrix 130 is formed such that an edge is shaped to conform to the contours of the interproximal gingival margin and in particular the edge which contacts the gum and is curved outwardly from the centre of the matrix to enable the matrix to be used to file deep cavities. The thickness of the matrix 130 is selected so that it is suitable for insertion inter-proximal between teeth 200/210. The thickness should be selected so that it provides sufficient rigidly to permit insertion without damage to the matrix 130. Preferably the matrix is between 0.2 and 0.7 millimeters.

Preferably the matrix 130 is made of stainless steel but brass or another suitable metal could be used. In an alternative embodiment, a clear matrix or matrix that transmits light could be used. Clear matrices have the advantage that they transmit light to assist in the curing of filling. A clear matrix could be made of polyester or other suitable plastic.

In embodiment preferred arrangement of the lugs, wedge and matrix all transmit light enabling light used to cure the filling to reach the filling material. This has the advantage of enabling the filling to cure faster and to ensure a more complete cure.

To assemble and use the contact matrix system of the present invention the dental professional first couples the lugs 110 to the respective ends 103a, 103b of the spring 101 (which mayor may not require a slight expansion of the spring arms 102a, 102b). The wedge is placed in the inter-proximal gingival margin and then the matrix 130 fitted about the inter-proximal space between the teeth 200/210 and round onto lingual/buccal sides of the tooth 200 to be filled. The wedge holds the matrix 130 in place while the retainer is placed next. The retainer comprising of spring 101 and lugs 110 is expanded at the arms 102a, 102b and placed about the tooth 200 to locate the lugs 110 at the interproximal space between the two teeth 200 and 210, on the lingual and buccal sides of the tooth 200 respectively. At this stage, the ends of the wedge are also located and inserted into the channels 117 of the lugs 110. The dental professional removes the expansion force on the arms 102a/b, and the lugs 110 are caused to move towards one another and clamp about the teeth 200/210 to hold the matrix 130 against the lingual and buccal sides of the tooth 200 under action of the bias provided by the spring. The lugs 110 and wedge press the matrix 130 against the tooth 200 surface from different directions thereby holding the matrix 130 in place.

It will be appreciated that the order of certain steps of the above method may be interchanged without departing from the scope of the invention, such as the lugs 110 may be fitted to the spring ends 103a, 103b after the wedge is placed, or the wedge may be fitted after placement of the matrix 130 and/or after placement of the retainer 100. During the procedure, the dental professional may change the wedge if it is of an inadequate size or for any other reason, by pulling the wedge out of the channels 117 and replacing it with another wedge of a similar or different size for example. The channels 117 are preferably deformable to accommodate wedges of various sizes should the professional require a change prior or mid procedure. Furthermore, in some embodiments two wedges may be placed on either side of tooth, one in each channel 117 if this is required. These may be of the same or different size as required for the particular procedure.

During the procedure, the dental professional can rotate the spring 101 about the lugs 110 to adjust the pivotal position of the spring 101, enabling the professional to conduct the procedure without obstruction from the spring 101, and without removing the clamping force provided by the retainer. The lugs remain in place as the spring is rotated. After the procedure, the professional can remove the retainer to release and remove the matrix 130 by expanding the arms 102*a/b* with a suitable tool, and may decouple the lugs 110 for cleaning and/or replacement before the next procedure.

The foregoing description of the invention includes preferred forms thereof. Modifications may be made thereto without departing from the scope of the invention as defined by the accompanying claims.

The invention claimed is:

1. A device for retaining a matrix band about at least a portion of a periphery of a tooth to be treated, the device comprising:
   a first lug to fit on a first side of a proximal contact between the tooth to be treated and an adjacent tooth,
   a second lug to fit on a second, opposite side of said proximal contact between the tooth to be treated and the adjacent tooth,
   a resilient body member connecting between said first lug and said second lug, said body member holding said first and second lugs such that said first and second lugs must be separated to fit over said first and second sides of the proximal contact, wherein the body member applies a restorative or clamping force biasing said first and second lugs together against said first and second opposed sides of said proximal contact, and
   each of the first and second lugs pivotally coupled to the resilient body member to allow the resilient body member to rotate relative to the first and second lugs about an axis substantially transverse to a tooth to be treated enabling the resilient body member to rotate between the mesial and distal sides of the tooth being treated while providing the clamping force biasing the first and second lugs together, wherein the first lug comprises a first socket for rotatably receiving a first associated inwardly extending end of the body member and second lug comprise a second socket for rotatably receiving a second associated inwardly extending end of the body member, wherein the first inwardly extending end of the body member and an inner periphery of the first lug socket comprise a corresponding formations for enabling a releasable engagement between the first body end and the first lug and wherein the second inwardly extending end of the body member and an inner periphery of the second lug socket comprise a corresponding formation-for enabling a releasable engagement between the second body end and the second lug, wherein the first inwardly extending end of the body member comprises a first annular detent about an outer periphery of the first inwardly extending end of the body member and the first lug comprises a corresponding first annular rib formed about an inner periphery of the first lug socket for engaging the associated first annular detent and wherein the second inwardly extending end of the body member comprises a second annular detent about an outer periphery of the second inwardly extending end of the body member and the second lug comprises a corresponding second annular rib formed about an inner periphery of the second lug socket for engaging the associated second annular detent.

2. The device of claim 1 wherein the body member is a U-shaped spring member having first and second separate and opposed ends at an opening of the Li-shaped member, the spring biasing the first and second ends together when the first and second ends are separated from a first, un-deflected position of the spring, each of the first and second lugs pivotally coupled to a respective first and second end of the spring.

3. The device of claim 1 wherein the body member is formed from a nickel-titanium alloy.

4. The device of claim 1 wherein the first lug comprises a first abutment surface for abutting against the matrix band at the corresponding side of the tooth to be treated and wherein the second lug comprises a second abutment surface for abutting against the matrix band at the corresponding side of the tooth to be treated.

5. The device of claim 4 wherein the first and second abutment surfaces are contoured to substantially conform to the periphery of corresponding sides of the tooth to be treated and an adjacent tooth and to the inter-proximal space between the tooth to be treated and the adjacent tooth.

6. The device of claim 5 wherein the first and second abutment surfaces each comprise a first intermediate ridge adapted to engage the inter-proximal space between the tooth to be treated and the adjacent tooth.

7. The device of claim 1 wherein the first and second lug each comprises a channel for receiving a dental wedge.

8. The device of claim 7 wherein the channel in each of the first and second lugs is formed to conform to the outer periphery of an end of the dental wedge to thereby enable opposing ends of the wedge to be received and retained within the channel of each lug when the lug is located against the matrix band in use and when the wedge is fitted in the inter-proximal space between the opposing sides of the tooth to be treated.

9. The device of claim 1 wherein the first and second lugs are formed from a polymer-based plastics material.

10. The device of claim 1 wherein the first and second lugs are formed from a transparent or semi-transparent material.

11. A device for retaining a matrix band about at least a portion of a periphery of a tooth to be treated, the device comprising:
   a first lug to fit on a first side of a proximal contact between the tooth to be treated and an adjacent tooth,
   a second lug to fit on a second, opposite side of said proximal contact between the tooth to be treated and the adjacent tooth,
   a resilient body member connecting between said first lug and said second lug, said body member holding said first and second lugs such that said first and second lugs must be separated to fit over said first and second sides of the proximal contact, wherein the body member applies a restorative or clamping force biasing said first and second lugs together against said first and second opposed sides of said proximal contact, and
   each of the first and second lugs pivotally coupled to the resilient body member to allow the resilient body member to rotate relative to the first and second lugs about an axis substantially transverse to a tooth to be treated enabling the resilient body member to rotate between the mesial and distal sides of the tooth being treated while providing the clamping force biasing the first and second lugs together, wherein the first lug comprises a first socket for rotatably receiving a first associated inwardly extending end of the body member and second lug comprise a second socket for rotatably receiving a second associated inwardly extending end of the body member, and wherein the first lug comprises, at the inner periphery of the first lug socket, at least a first flat surfaces for defining pivotal position limits, and wherein the corresponding first end of the body member comprises at least a first flat surfaces at the outer periphery for engaging with the corresponding at least a first flat surfaces of the first lug socket when the first end of the body member is received within the first lug socket and rotated to a pivotal position limit wherein the second lug comprises, at the inner periphery of the second lug socket at least a first flat surfaces for defining pivotal position limits, and wherein the corresponding second end of the body member comprises at least a first flat surfaces at the outer periphery for engaging with the corresponding at least a first flat surfaces of the second lug socket when the second end of the body member is received within the second lug socket and rotated to a pivotal position limit.

12. The device of claim 11 wherein the inner periphery of the first and second lug socket each comprises a first and second flat surfaces separated at less than 180 degrees about the inner periphery to define a first and second pivotal position limits of the body member less than 180 degrees apart during use.

* * * * *